(12) United States Patent
Maclaren et al.

(10) Patent No.: US 10,966,636 B2
(45) Date of Patent: Apr. 6, 2021

(54) DETERMINATION OF THE COORDINATE TRANSFORMATION BETWEEN AN OPTICAL MOTION TRACKING SYSTEM AND A MAGNETIC RESONANCE IMAGING SCANNER

(71) Applicant: The Board of Trustees of the Leland Stanford Junior University, Palo Alto, CA (US)

(72) Inventors: Julian Maclaren, Menlo Park, CA (US); Murat Aksoy, Menlo Park, CA (US); Melvyn B. Ooi, Tempe, AZ (US); Roland Bammer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 902 days.

(21) Appl. No.: 15/031,686

(22) PCT Filed: Dec. 2, 2014

(86) PCT No.: PCT/US2014/068125
§ 371 (c)(1),
(2) Date: Apr. 22, 2016

(87) PCT Pub. No.: WO2015/084826
PCT Pub. Date: Jun. 11, 2015

(65) Prior Publication Data
US 2016/0262663 A1     Sep. 15, 2016

Related U.S. Application Data

(60) Provisional application No. 61/910,915, filed on Dec. 2, 2013.

(51) Int. Cl.
*A61B 5/11* (2006.01)
*A61B 5/055* (2006.01)
(Continued)

(52) U.S. Cl.
CPC .......... *A61B 5/1114* (2013.01); *A61B 5/0555* (2013.01); *A61B 5/6803* (2013.01);
(Continued)

(58) Field of Classification Search
None
See application file for complete search history.

(56) References Cited

U.S. PATENT DOCUMENTS

| | | | |
|---|---|---|---|
| 5,545,993 A | | 8/1996 | Taguchi |
| 6,026,315 A | * | 2/2000 | Lenz .................... G01R 33/285 600/411 |

(Continued)

*Primary Examiner* — Bill Thomson
*Assistant Examiner* — Shahdeep Mohammed
(74) *Attorney, Agent, or Firm* — Lumen Patent Firm (57) ABSTRACT

Improved cross-calibration between magnetic resonance imaging (MRI) coordinates and optical tracking coordinates is provided. Initial calibration is performed with a calibration tool that includes wireless active markers that can be tracked using the MRI scanner, and an optical marker that can be tracked using the optical tracking system. Data from one or more poses of this tool are used to provide an initial cross-calibration. In use, this initial calibration is corrected to account for differences between actual camera position and the reference location. Here the reference location is the camera location at which the initial calibration was performed.

11 Claims, 5 Drawing Sheets

(51) Int. Cl.
*A61B 5/00* (2006.01)
*A61B 90/00* (2016.01)
*A61B 34/20* (2016.01)

(52) U.S. Cl.
CPC .............. *A61B 2034/2055* (2016.02); *A61B 2034/2065* (2016.02); *A61B 2090/3958* (2016.02); *A61B 2560/0223* (2013.01)

(56) References Cited

U.S. PATENT DOCUMENTS

| | | | |
|---|---|---|---|
| 6,351,659 B1* | 2/2002 | Vilsmeier | A61B 6/12 600/407 |
| 6,490,473 B1* | 12/2002 | Katznelson | A61B 5/055 600/410 |
| 6,493,574 B1* | 12/2002 | Ehnholm | A61B 5/055 378/18 |
| 2005/0054910 A1 | 3/2005 | Tremblay | |
| 2007/0034731 A1* | 2/2007 | Falco | G01B 7/008 244/3.1 |
| 2009/0209846 A1 | 8/2009 | Bammer | |
| 2010/0228117 A1* | 9/2010 | Hartmann | A61B 5/06 600/424 |
| 2011/0230755 A1 | 9/2011 | MacFarlane | |
| 2012/0078236 A1* | 3/2012 | Schoepp | A61B 5/061 606/1 |
| 2013/0188830 A1 | 7/2013 | Ernst | |

\* cited by examiner

DETERMINATION OF THE COORDINATE TRANSFORMATION BETWEEN AN OPTICAL MOTION TRACKING SYSTEM AND A MAGNETIC RESONANCE IMAGING SCANNER

CROSS-REFERENCE TO RELATED APPLICATIONS

This application is a 371 of PCT/US2014/068125 filed Dec. 2, 2014. PCT/US2014/068125 claims the benefit of U.S. Provisional Application 61/910,915 filed Dec. 2, 2013.

STATEMENT OF GOVERNMENT SPONSORED SUPPORT

This invention was made with Government support under contract EB011654 awarded by the National Institutes of Health. The Government has certain rights in the invention.

FIELD OF THE INVENTION

The present invention relates to medical imaging. It involves the calibration of an optical tracking device that is used for motion tracking of a human or animal subject during simultaneous magnetic resonance imaging. More specifically, it allows for the calculation of a coordinate transformation between the coordinate system of the optical tracking device and the coordinate system of the MRI scanner.

BACKGROUND

Magnetic resonance imaging (MRI) is a valuable medical imaging technique for humans and animals. MRI is often used for imaging the human body, both for research and for clinical purposes, such as the diagnosis of numerous diseases and for surgical planning.

Magnetic resonance imaging is typically performed with the patient lying in a long narrow bore and with body part under interrogation located in a confined coil, which is used to receive signal for image reconstruction. A single scan lasts on the order of minutes; the entire exam typically consists of several scans and lasts on the order of tens of minutes. During an MRI scan it is necessary for the patient to remain nearly motionless, as translational movements of only a few millimeters or rotations of a few degrees can result in severe motion artifacts in the reconstructed images. Many patients have difficulty with this requirement, particularly the elderly, children, or those who suffer from claustrophobia.

U.S. Pat. No. 5,545,993 describes how a motion tracking system can be used to prevent motion artifacts during magnetic resonance imaging by updating the imaging magnetic fields to compensate for the measured motion. This procedure is now widely known under the terms 'prospective motion correction' or 'adaptive motion correction'. Optical tracking is a popular method for obtaining the required motion information from the subject. Optical systems, such as cameras, are independent from the normal MRI image acquisition and therefore the procedure requires minimal modification to the MRI pulse sequence. Camera-based systems can operate at high temporal resolution (e.g. 30 Hz or more), which is sufficient to sample and correct for movements made by human subjects during MRI.

One challenge with camera-based systems is that the camera's frame of reference is not automatically aligned with that of the MRI scanner. That is, motion parameters obtained with an optical system are specified in the coordinate system of the optical tracking system and not in the coordinate system of the MRI scanner. Thus, tracking data must be transformed from the camera's frame of reference into the MRI scanner's frame of reference using a transformation that consists of rotations and translations. This transformation is often stored in a single matrix, in which case it is referred to as a homogeneous transformation matrix. The process of determining the entries in this transformation matrix is widely referred to as 'cross-calibration'. Such cross-calibration has been considered in U.S. Pat. No. 6,490,473.

Although previous works describe how to obtain an accurate cross-calibration, the methods used are often not practical for clinical deployment of an optical motion correction system in MRI. In particular, conventional approaches provide no means to (a) quickly (<2 minutes) obtain a cross-calibration good enough for accurate motion correction without an initial estimate of the calibration and (b) maintain cross-calibration accuracy even when the optical tracking system is moved or repositioned, such as when it is attached to a moveable head coil and the placement on the patient table changes from patient to patient, or when the patient table is moved during an MRI examination.

SUMMARY

This work addresses the need for calibration discussed above, i.e. (a) a fast initial calibration and (b) a recalibration if the patient table, head coil, and/or camera system are moved/repositioned. In the following, 'cross-calibration' refers to the process of determining an approximate coordinate transformation between two frames of reference.

This work provides a one-time, highly accurate means to perform cross-calibration. A calibration tool is employed, which includes wireless active markers visible to the MRI system and an optical marker visible to the optical system that is being calibrated. The position and orientation of the wireless active markers are tracked using the MRI scanner: the tracking data from these wireless markers are inherently registered in the coordinate system of the MRI system. The wireless active markers are rigidly connected to an optical marker, such that both marker systems always experience the same motion and have a fixed (but not necessarily known) geometric relationship to each other.

An exemplary method for cross-calibration using the calibration tool proceeds as follows: a single quick tracking scan is performed, during which a series of small rotations are performed to the calibration tool. During this time, motion data are collected from both the wireless active markers (using the MRI scanner tracking pulse sequence) and from the optical marker (using the optical tracking system). A series of 'poses' are then extracted from the tracking data, for both the optical and active marker tracking systems at the same physical location of the calibration tool. From this, a series of 'motions' between successive poses is calculated for each of the two tracking systems. A transformation is then calculated from the optical coordinate system to the active marker coordinate system, such that the motion from one pose to the next is as consistent as possible.

Typically the optical tracking system includes at least a first camera, and the position of this first camera can change from one scan to the next. Accordingly, the above-described initial calibration is performed with the first camera disposed at a reference location, and this initial calibration is corrected as needed to account for any difference between the actual position of the camera and the reference location. In some cases, a second camera is used to determine the location of the first camera relative to the reference location. Correcting the initial calibration to account for the new camera position is much less time consuming than redoing the initial calibration, so this two-step process provides significantly reduced cross-calibration times in practice.

DETAILED DESCRIPTION

Figure 1:
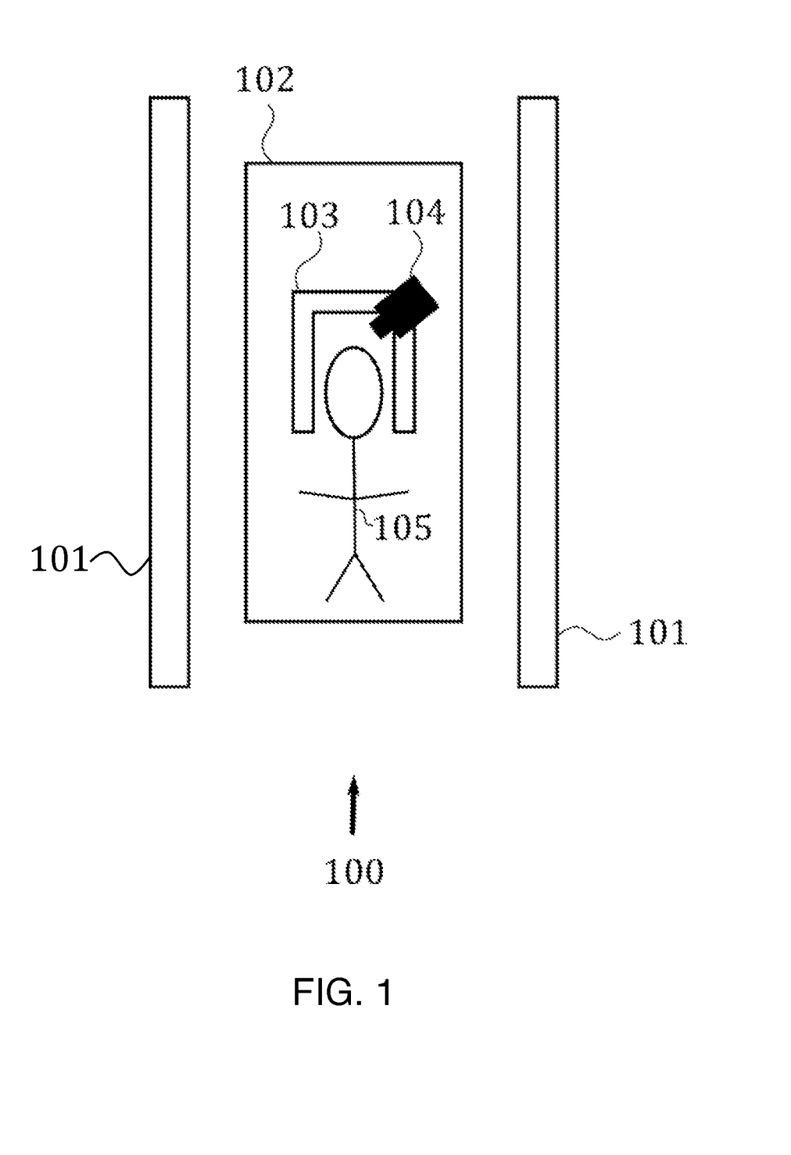
FIG. 1 shows how an MR-compatible camera is placed on a head coil inside an MRI scanner to track the head motion of a patient lying on the patient table.

FIG. 1 shows an MRI system 100 including an MRI scanner 101, and a patient table/couch 102, where the subject 105 lies during an MRI examination. In this example, the head of the subject is placed inside a head coil 103 and head motion is monitored using a camera 104. The main objective of this work is to provide a practical means to calculate the transformation between the coordinate system of the camera 104 and the coordinate system of the MRI scanner 101.

Figure 2:
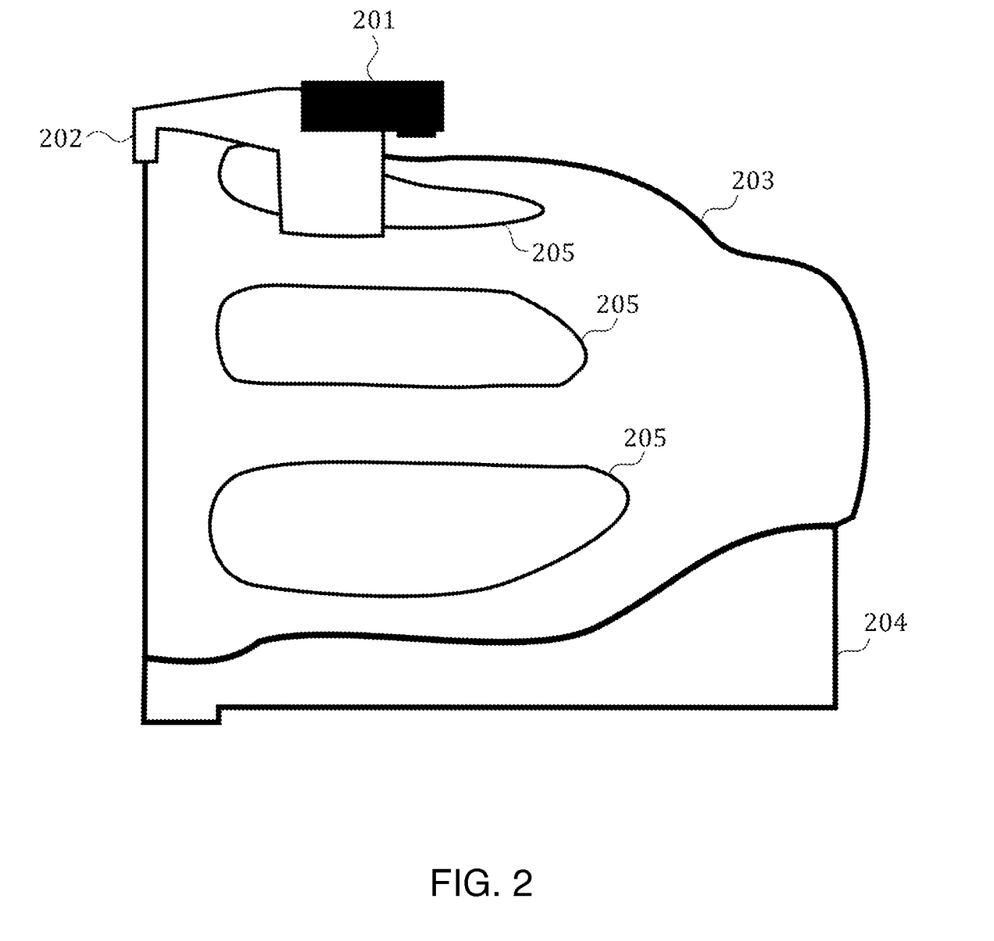
FIG. 2 shows an example of a camera rigidly attached to a MRI scanner head coil, so that no motion can occur between the two components.

FIG. 2 shows an example of a camera 201, which is attached to the head coil 203 using a rig 202 that has been designed to snugly fit to the head coil. The rig ensures that the camera and head coil form a rigid body, namely that they move together as a single object. The head coil is placed on a removable base 204, which is attached to the patient table. Holes in the head coil 205 provide a line of sight from camera 201 to the head of the subject. Alternatively, the camera can be integrated with the MRI head coil assembly.

Figure 3A:
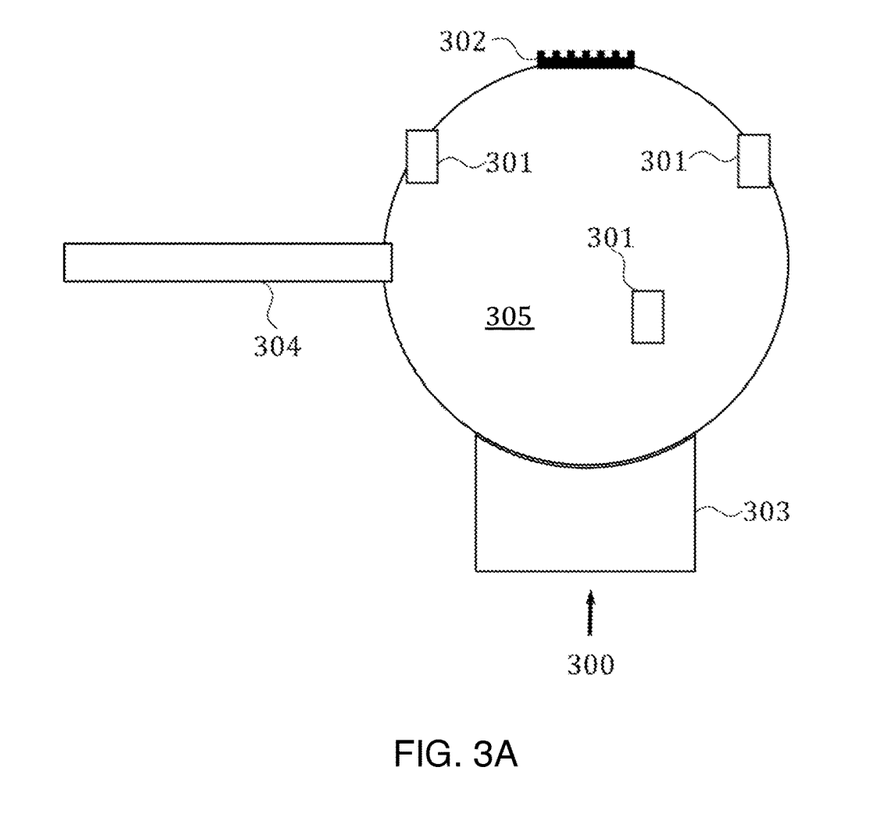
FIG. 3A shows a calibration tool including three 'wireless markers' and an optical tracking marker.

FIG. 3A shows an exemplary calibration tool 300 that comprises three wireless active markers 301 and an optical marker 302. The wireless markers can be enclosed within polycarbonate boxes, which helps protect them against physical damage and detuning. The calibration tool can be manually rotated using a plastic handle 304. This calibration tool is configured as a spherical member 305 disposed in a receptacle 303 that provides mechanical support while allowing the tool to be moved to various orientations.

In a preferred embodiment, the calibration tool can be rotated easily about all three axes, such that the center of rotation remains close to the isocenter of the MRI scanner. Keeping the calibration device near the isocenter helps ensure that tracking with both systems is accurate.

In a preferred embodiment, the calibration tool includes a plastic handle 304, which the operator or a mechanical actuator can use to conveniently rotate the calibration tool, while maintaining a distance of at least 10 cm from the calibration tool. This prevents any interaction (through magnetic field disturbances) between the operator and the wireless active markers.

Figure 3B:
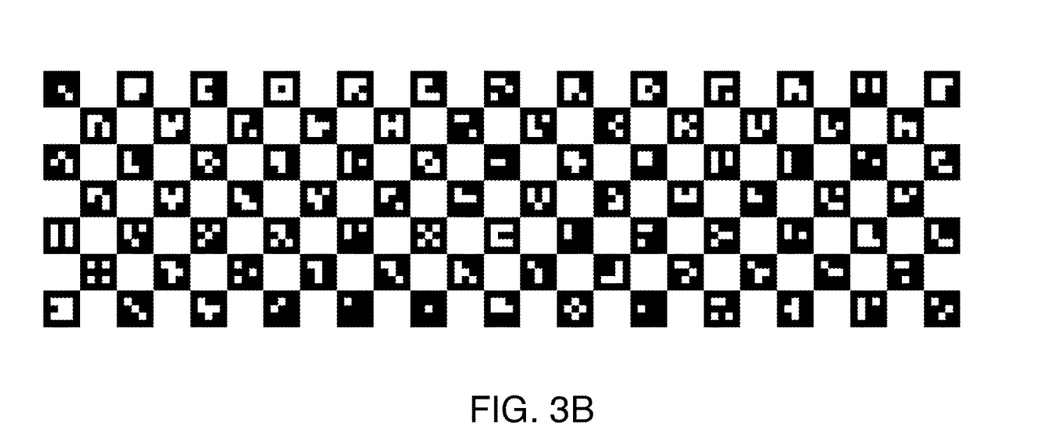
FIG. 3B shows an exemplary optical tracking marker for the calibration tool.

FIG. 3B shows an example of a preferred configuration for optical marker 302. Here the optical features of marker 302 are individually distinguishable, and are arranged in a predetermined pattern having known relative positions. The result of this is that partial observation of the pattern suffices to completely determine the position of the optical marker. For example, if a checkerboard pattern of 5 white dots is observed, it would be known that this feature is in the 5th row (from the top) and 11th column (from the left) of this pattern. It is preferable for the features to be chosen such that they remain distinct in the presence of 90-degree rotations. The example of FIG. 3B has this property. Further details relating to this kind of optical marker pattern are described in U.S. Pat. No. 8,848,977, hereby incorporated by reference in its entirety.

In an exemplary embodiment, a method of cross-calibrating magnetic resonance imaging (MRI) coordinates with coordinates of an optical tracking system includes the following steps: 1) performing an initial calibration by measuring MRI and optical coordinates of a calibration tool while a first camera of the optical tracking system is disposed at a reference location; and 2) correcting the initial calibration before or during MRI imaging of a subject to account for any difference between the current position of the first camera and the reference location of the first camera.

The calibration tool for the initial calibration includes optical features recognizable by the optical tracking system. The calibration tool also includes wireless active MRI markers recognizable by the MRI system.

The optical features and the wireless active MRI markers have fixed relative positions on the calibration tool. However, these relative positions need not be known in advance.

The initial calibration includes taking MRI and optical data for one or more distinct poses (where a 'pose' is the combination of position and orientation) of the calibration tool and determining an initial cross-calibration coordinate transformation relating MRI coordinates to optical coordinates. In cases where the fixed relative positions of the optical features and the wireless active markers on the calibration tool are known as inputs for the initial calibration, data from a single pose of the calibration tool may suffice. If these relative positions are not known, then data from three or more poses of the calibration tool will be needed to determine the initial calibration.

Correcting the initial calibration includes: 1) determining a position of the first camera relative to the reference location; 2) determining a corrected calibration using the camera position and the initial cross-calibration coordinate transformation; and 3) using the corrected calibration to relate MRI coordinates to optical coordinates for the subject being imaged.

Preferably each wireless active MRI marker includes an MR-visible sample coupled to a resonant circuit. With this arrangement, positions of the wireless active MRI markers can be determined by the MRI system via inductive coupling of the resonant circuits of the wireless active MRI markers to one or more receive coils of the magnetic resonance system. Further details relating to such wireless active markers are described in US 2014/0171784, hereby incorporated by reference in its entirety.

In a preferred embodiment, the method for initial cross-calibration using the calibration tool involves stepwise motion that includes short stationary periods. During these periods tracking data are averaged by the calibration algorithm to reduce the effects of tracking noise. In this way, it is possible to obtain high quality tracking data with the calibration tool in a large number of different poses (e.g. 20). This number of poses is sufficient to achieve accurate cross calibration. This also allows for the use of an automated calibration procedure where the calibration tool is mounted on a computer-controlled rotational stage for performing highly precise motion maneuvers for calibration.

In another embodiment, the geometric relationship between the optical marker and the wireless active markers is known in advance. That is, the optical marker and the wireless markers are placed on the calibration tool in known positions. In this case, data from a single pose are sufficient to determine the transformation matrix between the optical tracking coordinate system and the MRI coordinate system, reducing the calibration time to less than 500 ms.

Suitable methods for determining the cross-calibration from the optical and MRI data collected from the calibration tool poses are known in the art. In general, these methods are referred to as hand-eye calibration methods. For example, the application of one such method to MRI is described by Zahneisen et al. in an article entitled "Fast noniterative calibration of an external motion tracking device" (Magnetic Resonance in Medicine, v71n4, pp. 1489-1500, 2014), hereby incorporated by reference in its entirety.

The present approach using wireless markers allows very high speed (e.g. 20 Hz or faster) tracking of the pose of the calibration tool. This offers a huge practical advantage relative to the hand-eye calibration method in Zahneisen, where each pose is obtained by scanning a phantom, which takes around 2 minutes. As a minimum, three distinct poses are required, giving two distinct non-parallel motions between poses.

In summary, the methods as described above give the ability to perform a fast initial calibration that provides an accurate transformation matrix that relates the optical frame of reference defined by the camera and its orientation (at the camera reference location) relative to the MR frame of reference defined by the gradient system of the MRI scanner. The following description provides examples of correcting the coordinate transformation to account for camera locations that deviate from the reference location, and examples of various ways to determine the required camera position information.

One important special case is determining z-position of the camera. Here, as usual, the z-direction is along the bore of the MRI system. The z-offset can be determined from a position encoding of a patient table of the MRI system.

If the optical system needs to be removed/repositioned from the MRI scanner or the patient couch, then it is desirable to reinstall it later without having to repeat the initial calibration procedure described above. Our experiments indicate that the camera can be removed and reproducibly repositioned within +/−0.5 mm in the x and y directions, and to within +/−0.5 degrees of rotation about x, y and z. This is achievable by securely mounting the camera on the head coil using a rigid attachment. The only degree of freedom that is not reproducible is z, which corresponds to the patient head-feet direction. Repositioning in this direction is not reproducible because that is the direction of motion of the patient table. In other words, if the camera is taken out of the scanner, it can be easily returned to the same place later, except for a shift in the head-feet (z) direction.

Due to the above, it is therefore possible to maintain a correct camera calibration after removing and then reinstalling the camera, if the unknown repositioning error in the z-direction is accounted for. This can be achieved using the following method.

The result of the initial cross calibration is a 4-by-4 homogeneous transformation matrix, H. This homogenous transformation matrix includes a 3-by-3 rotation matrix, R, and a 3-by-1 translation vector v, i.e., $$H = \begin{bmatrix} R & v \\ (000) & 1 \end{bmatrix}$$

and where the translation vector, v, contains three components $$v = \begin{bmatrix} x \\ y \\ z' \end{bmatrix},$$

and x, y, and z described the shift from the origin of the MRI scanner coordinate system to the origin of the optical tracking coordinate system in the scanner x, y and z directions, respectively. Similarly, the rotation matrix R describes the rotation of the optical tracking coordinate system relative to the scanner coordinate system. As an example, a typical matrix H could be $$H = \begin{bmatrix} 0.92 & -0.02 & 0.40 & -47.84 \\ 0.40 & 0.04 & -0.92 & -189.05 \\ -0.00 & 1.00 & 0.04 & 5.25 \\ 0 & 0 & 0 & 1 \end{bmatrix},$$

where the three numbers in column 4, rows 1-3, correspond to a camera frame of reference that is located 47.84 mm, 189.05 mm and 5.25 mm away from the scanner isocenter in the x, y and z directions respectively.

In a preferred embodiment, the 'position encoder' that is part of the patient table mechanism returns a value indicating the table position in the z direction. When the initial calibration is performed, this value, $t_{z0}$, is recorded, along with the calculated transformation matrix. Whenever the camera is reinstalled, or the table is moved, a new value, $t_{z1}$, is obtained from the position encoder. The translation vector component of the transformation matrix is then updated such that z, the component of the translation vector describing the shift in the z direction is replaced with z', i.e., $$v = \begin{bmatrix} x \\ y \\ z' \end{bmatrix},$$

where $z'=z+(t_{z1}-t_{z0})$.

In another embodiment, the position information (i.e. $t_{z0}$ and $t_{z1}$) is obtained via a laser ranging system or interferometer that tracks the patient table. The RF coil, or the camera, can also be tracked directly using a laser ranging or interferometer-based approach. Again, degrees of freedom other than z can be handled by using a rig that ensures accurate repositioning of the camera in these other degrees of freedom.

Figure 4:
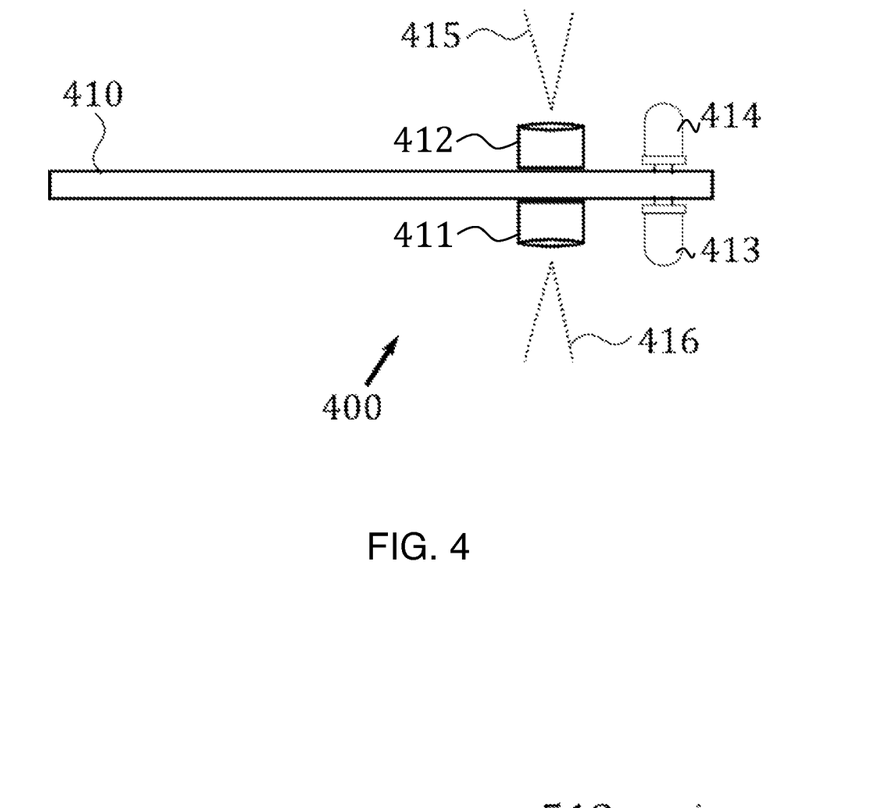
FIG. 4 shows a camera unit that comprises two individual cameras: one facing inwards, towards the subject, and one facing outwards, towards the inner wall of the MRI scanner bore.

In another embodiment, the position information is obtained via the camera system itself. In this embodiment, the camera board includes one inwards-facing camera and one outwards-facing camera, where the geometric relation to each other is known. In this way the camera can track both subject motion and the position of a fixed position marker attached to the MRI bore and visible, but not limited, to the outwards-facing camera. FIG. 4 shows an example of this approach. Tracking system 400 includes a two-way camera board 410 designed to simultaneously track both subject motion and the position of the camera itself by monitoring the position of a marker on the inner wall of the scanner bore, which is known to be stationary. The camera board includes one inward-facing camera 411 (field of view referenced as 416), one outward-facing camera 412 (field of view referenced as 415), and corresponding LEDs (413 and 414), which provide illumination of the subject and the scanner bore, respectively. The relative position of cameras 411 and 412 is known.

Figure 5:
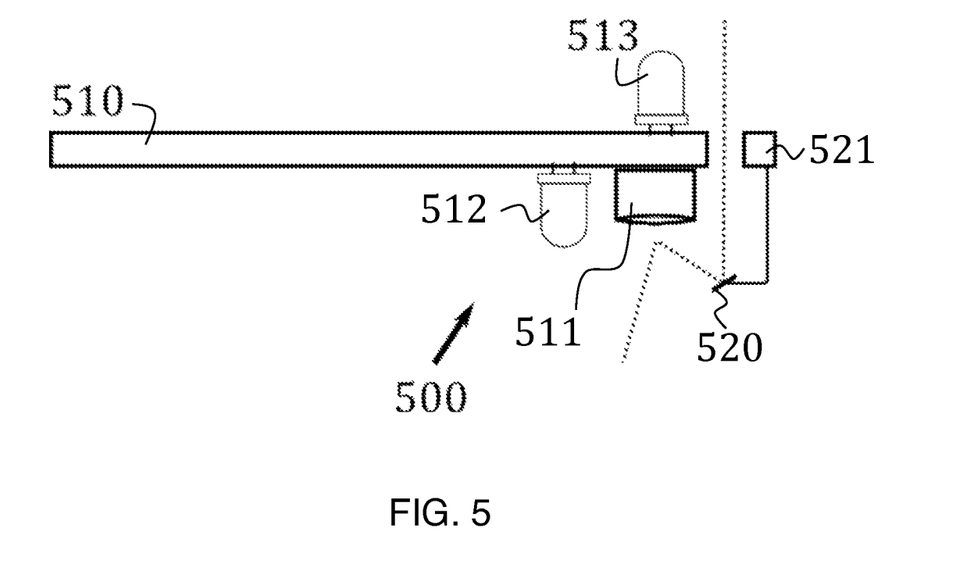
FIG. 5 shows a camera unit that comprises one camera and a small mirror to allow simultaneous view of the subject and the inner wall of the MRI scanner bore.

In another embodiment, the camera unit contains a single camera, but also a (optionally retractable) mirror that lies in the field of view of the camera. This mirror allows the camera to track a marker that lies behind it on the scanner bore while the camera simultaneously tracks subject motion. FIG. 5 shows an example of this approach. Here tracking system 500 includes a two-way board 510 that requires only a single camera 511. Illumination is provided in both the inwards and outwards direction using two LEDS (512 and 513, respectively). A small mirror 520 that lies in the field of view of the camera provides a line of sight behind the camera, which is used to track a marker mounted on the inner wall of the scanner bore. The mirror 520 and camera 511 are attached to one another using a rigid connection 521, such that they cannot move independently from one another.

Figure 6:
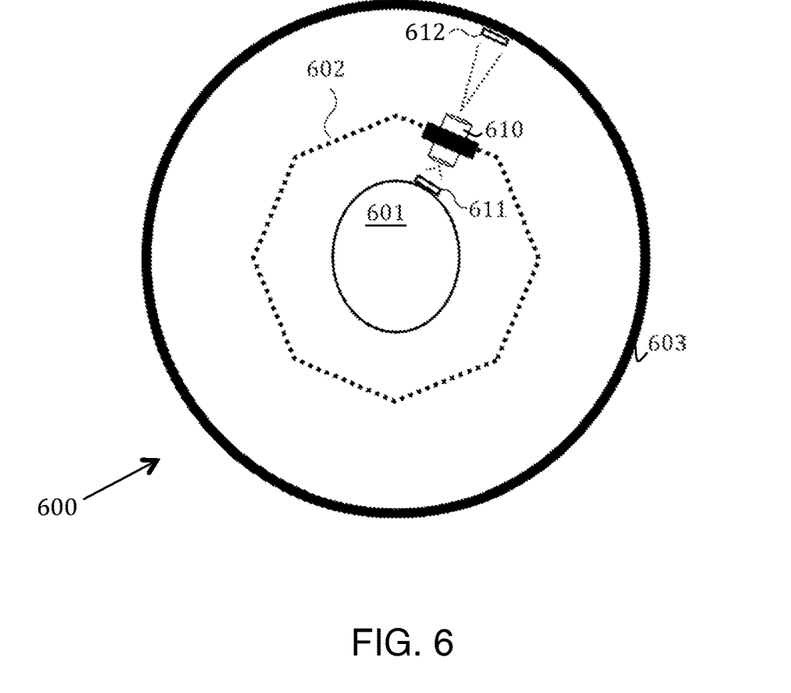
FIG. 6 shows how the camera units illustrated in FIG. 4 and FIG. 5 can track a marker mounted on the subject, while simultaneously determining their own position within the scanner by tracking a marker mounted on the scanner.

FIG. 6 shows how the two-way camera unit shown in FIGS. 4 and 5 can be used for simultaneous tracking of subject motion and adjustment of the camera-scanner transformation matrix. The subject 601 lies within the RF coil 602, which is within the bore 603 of the stationary MRI scanner 600. The camera unit 610 tracks a marker mounted on the subject 611 using the inward-facing camera. Tracking with the inward-facing camera operates at a rate of 30 Hz or greater and in six degrees of freedom, to fully capture the motion of the subject. Using the outward-facing camera, the camera unit 610 tracks a bore optical marker 612 mounted on the inner wall of the scanner bore. This enables the position of the camera to be calculated with respect to the scanner bore. The outward-facing camera can operate at rates much lower than 30 Hz, as the head coil and camera unit are only moved occasionally, for example during repositioning of the patient table. The outward-facing camera and bore optical marker 612 are often used only to measure the position of the camera unit in the z-direction, since the patient table and head coil often only have freedom to move in this direction.

Here a bore optical marker is affixed to the bore of the MRI system at a known position relative to the reference location. Determining a position of the first camera relative to the reference location includes observing the bore optical marker with the optical tracking system.

In a further embodiment, a second camera is fixed permanently and rigidly to the scanner bore and is already calibrated relative to the scanner, using one of the methods described here. This second camera monitors the position and orientation of a marker rigidly attached to the case of the first camera, mounted on the RF coil. In this way, the first camera can be moved after its cross-calibration procedure is performed and the transformation matrix can be adjusted, based on the position of the marker as seen by the second camera. Here the second camera is affixed to the bore of the MRI system at a known position relative to the reference location, and determining a position of the first camera relative to the reference location includes observing an optical marker affixed to the first camera with the second camera.

Figure 7:
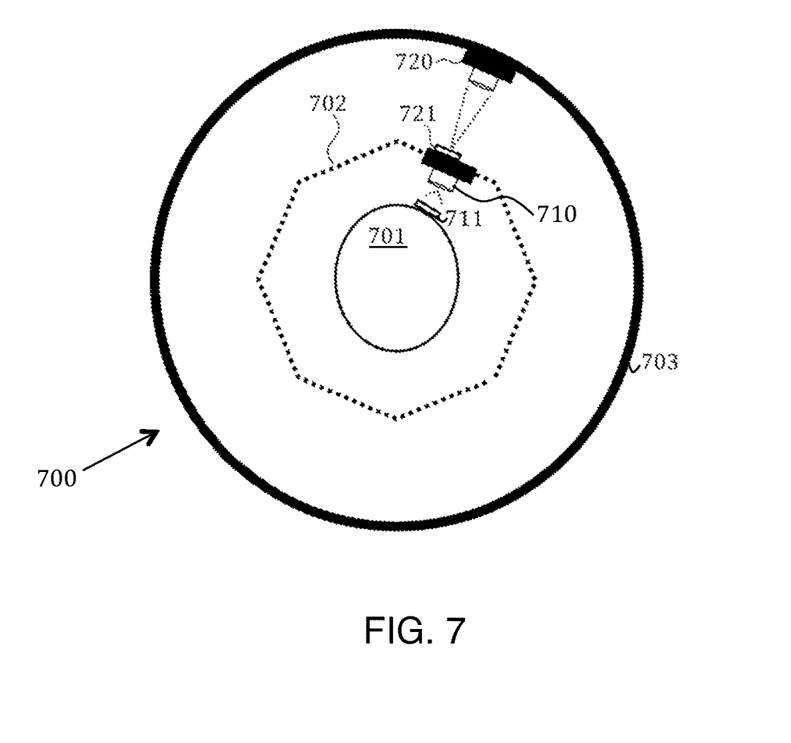
FIG. 7 shows an example where a bore-mounted camera views an optical marker on the tracking camera to provide camera position information of the tracking camera.

FIG. 7 shows an example of this approach. The subject 701 lies within the RF coil 702, which is within the bore 703 of the stationary MRI scanner 700. The first camera unit 710 tracks an optical marker 711 mounted on the subject 701. A second camera 720 is mounted on the inside of the scanner bore 703 and tracks an optical marker 721 mounted on the first camera. This allows changes in the position of the first camera 710 relative to the MRI scanner to be measured. The cross-calibration transformation matrix of the first camera can then be adjusted accordingly.

In a further embodiment, wireless active markers (or galvanically connected markers) are attached to the camera case or the RF coil. The wireless marker tracking pulse sequence is then used to determine the position and orientation of the camera in the coordinate system of the MRI scanner. If three or more markers are used, all six degrees of freedom of the coordinate transform can be calculated. However, only a single marker is required to determine the position of the camera system in the z direction, and the transformation matrix can be updated as described above. The markers contain samples of low MR visibility (e.g. silicone, rather than gadolinium doped water). This ensures that they generate enough signal for tracking but are not visible on the MR images. Here an MRI-visible camera marker is affixed to the first camera, and determining the position of the first camera relative to the reference location includes determining the position of the MRI-visible camera marker using the MRI system.

The invention claimed is:

1. A method of cross-calibrating magnetic resonance imaging (MRI) coordinates with coordinates of an optical tracking system in an MRI system, the method comprising:
   a) providing a calibration tool, wherein the calibration tool includes optical features recognizable by the optical tracking system, wherein the calibration tool includes wireless active MRI markers recognizable by the MRI system, wherein the optical features and the wireless active MRI markers have fixed relative positions on the calibration tool;
   b) performing an initial calibration by measuring MRI and optical coordinates of the calibration tool while a first camera of the optical tracking system is disposed at a reference location, wherein the first camera is attached to a head coil of the MRI system;
   wherein the initial calibration comprises taking MRI and optical data for one or more distinct poses of the calibration tool and determining an initial cross-calibration coordinate transformation relating MRI coordinates to optical coordinates;
   c) before or during imaging of an MRI subject, i) determining a position of the first camera relative to the reference location, ii) determining a corrected calibration using the camera position and the initial cross-calibration coordinate transformation by updating a homogenous transformation matrix of the initial cross-calibration with a position change of the first camera, and iii) using the corrected calibration to relate MRI coordinates to optical coordinates for the subject being imaged;

wherein the initial cross-calibration can be represented by the homogenous transformation matrix $$H = \begin{bmatrix} R & v \\ (0,0,0) & 1 \end{bmatrix},$$

wherein R is a 3 by 3 rotation matrix of the initial cross-calibration, wherein v is a 3 by 1 translation vector of the initial cross-calibration, and wherein the homogenous transformation matrix of the corrected calibration is given by, $$H' = \begin{bmatrix} R & v' \\ (0,0,0) & 1 \end{bmatrix},$$

wherein $v^1$ is a 3 by 1 translation vector relating to the position change of the first camera.

2. The method of claim 1, wherein each wireless active MRI marker includes an MR-visible sample coupled to a resonant circuit, and wherein positions of the wireless active MRI markers can be determined via inductive coupling of the resonant circuits of the wireless active MRI markers to one or more receive coils of a magnetic resonance system.

3. The method of claim 1, wherein the optical features are individually distinguishable, and wherein the optical features are arranged in a predetermined pattern having known relative positions, whereby partial observation of the pattern suffices to completely determine a position of the optical marker.

4. The method of claim 1, wherein an MRI-visible camera marker is affixed to the first camera, and wherein the determining a position of the first camera relative to the reference location comprises determining a position of the MRI-visible camera marker using the MRI system.

5. The method of claim 1, wherein a bore optical marker is affixed to a bore of the MRI system at a known position relative to the reference location, and wherein the determining a position of the first camera relative to the reference location comprises observing the bore optical marker with the optical tracking system.

6. The method of claim 1, wherein a second camera is affixed to a bore of the MRI system at a known position relative to the reference location, and wherein the determining a position of the first camera relative to the reference location comprises observing an optical marker affixed to the first camera with the second camera.

7. The method of claim 1, wherein the fixed relative positions of the optical features and the wireless active markers on the calibration tool are known inputs for the initial calibration.

8. The method of claim 1, wherein a z-direction is along a bore of the MRI system, and wherein the determining a position of the first camera relative to the reference location comprises determining a z-offset of the camera.

9. The method of claim 8, wherein the z-offset is determined from a position encoding of a patient table of the MRI system.

10. The method of claim 1, wherein the initial calibration comprises taking MRI and optical data for three or more distinct poses of the calibration tool, thereby providing two or more distinct motions that are used for calibration.

11. The method of claim 10, wherein the initial calibration is computed without a priori knowledge of the fixed relative positions of the optical features and the wireless active markers on the calibration tool, and wherein the fixed relative positions of the optical features and the wireless active markers on the calibration tool are determined from the three or more distinct poses of the calibration tool.

* * * * *